(12) United States Patent
Apkarian

(10) Patent No.: US 8,653,120 B2
(45) Date of Patent: Feb. 18, 2014

(54) METHOD FOR TREATMENT OF CHRONIC NEUROPATHIC PAIN

(75) Inventor: A. Vania Apkarian, Chicago, IL (US)

(73) Assignee: Apkarian Technologies LLC, Chicago, IL (US)

( * ) Notice: Subject to any disclaimer, the term of this patent is extended or adjusted under 35 U.S.C. 154(b) by 61 days.

(21) Appl. No.: 12/326,107

(22) Filed: Dec. 2, 2008

(65) Prior Publication Data
US 2009/0118341 A1 May 7, 2009

Related U.S. Application Data

(62) Division of application No. 10/907,149, filed on Mar. 22, 2005, now abandoned.

(60) Provisional application No. 60/555,264, filed on Mar. 22, 2004.

(51) Int. Cl.
*A01N 43/80* (2006.01)
*A61K 31/42* (2006.01)
*A01N 43/08* (2006.01)
*A61K 31/34* (2006.01)

(52) U.S. Cl.
USPC ............................ 514/380; 514/378; 514/472

(58) Field of Classification Search
USPC .......................................... 514/380, 378, 472
See application file for complete search history.

(56) References Cited

U.S. PATENT DOCUMENTS

| 5,627,168 | A | * | 5/1997 | Bigge et al. ...................... 514/85 |
| 6,228,875 | B1 | | 5/2001 | Tsai |
| 7,846,913 | B2 | | 12/2010 | McDevitt |

FOREIGN PATENT DOCUMENTS

| WO | WO 01/36423 | 5/2001 |
| WO | WO 03/089411 | 10/2003 |
| WO | WO 2005/092442 | 10/2005 |

OTHER PUBLICATIONS

Young, D. The American Society of Health-System Pharmacists. 2002, Guidelines Promote COX-2 inhibitors for Managing Chronic Pain. pp. 1-4.*
Krystal et al., NMDA agonists and antagonists as probes of glutamatergic dysfunction and pharmacotherapies in neuropsychiatric disorders, 1999, Publisher: President and Fellows of Harvard College.
Millan et al., (+)-HA 966, a partial agonist at the glycine site coupled to NMDA receptors, blocks formalin-induced pain in mice, European Journal of Pharmacology, 1993 pp. 445-447, vol. 238, Publisher: Elsevier Science Publishers B.V.
Millan et al., Chemically-diverse ligands at the glycine B site coupled to N-methyl-D-aspartate (NMDA) receptors selectively block the, Neroscience Letters, 1994, pp. 139-143, No. 178, Publisher: Elsevier.
Parsons et al., Modulation of NMDA receptors by glycine—introduction to some basic aspects and recent developments, Amino Acids, 1998, pp. 2007-2016, No. 14, Publisher: Springer Verlig, Published in: Austria.
PCT/IB2005/050983 International Search Report, Oct. 12, 2005.
PCT/IB2005/050983 IPRP, Sep. 26, 2006.
PCT/IB2005/050983 Written Opinion, Sep. 22, 2006.
Tsai G et al: "Glycine Transporter Inhibitor, N-Methyglycine (Sacrosone), Added to Antipsychotics for the treatment of schizophrenia" Biological Pshychiatry, Elsevier Sicience, New York, NY, US vol. 55, No. 5, (Mar. 1, 2004) p. 452-456.
Mutschler: "Arzneimittelwirkugen" 2001, WWG, Stuttgart, XP002347156.
Cohen et al. Opiate Receptor Avidity and Cerebral blood flow in Alzheimer's disease. 1997, Journal of Neurological sciences. vol. 148, pp. 171-180.
Koichi Tan-No et al., Intrathecally Administered D-Cycloserine Produces Nociceptive Behavior Through the Activation of N-Methyl-D-aspartate Receptor Ion-Channel Complex Acting on the Glycine Recognition Site. Apr. 24, 2007, Journal of Pharmacological Sciences. vol. 104, pp. 39-45.
Koichi Tan-No et al., Intrathecally Administered spermine produces the scratching, biting and licking behavior in mice. 2000. Pain. vol. 86, pp. 55-61.
Wolf, Clifford J., Pain: Moving from Symptom Control toward mechanism-Specific Pharmacologic Management. Mar. 16, 2004. Annuals of Internal Medicine. vol. 140 No. 6, pp. 441-451.
Henderson et al., "Competitive antagonists and partial agonists at the glycine modulatory site of the mouse N-methyl-D-aspartate receptor," *J. Physiol.* 430:189-212 (1990) (English Abstract Only).
Lauritzen, "Spreading depression and migraine," *Pathol. Biol. (Paris)* 40:332-337 (1992) (English Abstract Only).
Pauwels et al., "Ca++ and Na+ channels involved in neuronal cell death. Protection by flunarizine," *Life Sci.* 48:1881-1893 (1991) (English Abstract only).
Le Bars et al., "Animal models of nociception," Pharmacol Rev. 53(4):597-652 (2001).

* cited by examiner

*Primary Examiner* — Samira Jean-Louis

(74) *Attorney, Agent, or Firm* — Clark & Elbing LLP; Karen L. Elbing

(57) ABSTRACT

Chronic pain is treated in an individual suffering from chronic pain by administering to the individual an amount of a therapeutic containing a glycine receptor agonist such as D-cycloserine or a GlyT-1 glycine transporter antagonist such as sarcosine in an amount effective to treat the chronic pain. The therapeutic may also contain a secondary analgesic such as opiates, NSAIDs or cox-2 inhibitors. The analgesic can be formulated in a pharmaceutical composition in the form of an injectable solution that contains at least two different analgesics, at least one of the analgesics of which is a glycine receptor agonist or a GlyT-1 glycine transporter antagonist. Suitable pharmaceutical compositions contain D-cycloserine and/or sarcosine, optionally in combination with opiates, NSAIDs or cox-2 inhibitors.

20 Claims, 5 Drawing Sheets

METHOD FOR TREATMENT OF CHRONIC NEUROPATHIC PAIN

STATEMENT OF RELATED APPLICATIONS

This application is a divisional of U.S. application Ser. No. 10/907,149, filed Mar. 22, 2005, which application claims the benefit of U.S. application No. 60/555,264, filed Mar. 22, 2004, both of which applications are incorporated herein by reference for all purposes.

STATEMENT CONCERNING GOVERNMENT FUNDING

This invention was made in part with funds from NIH Grants Nos. NS 35115 and NS 42660. The United States Government may have certain rights in the invention.

BACKGROUND OF THE INVENTION

This application relates to the use of glycine receptor agonists and glycine transporter antagonists for the treatment of chronic pain.

Treatment of chronic pain is a challenge for physicians and patients since there are no medications that specifically target the condition, and since the medications presently used result in very little relief and are based on their efficacy in acute pain conditions or on their efficacy on relieving secondary effects like anxiety and depression. Incidence of chronic pain is increasing in society and its burden on society is huge in both health care and lost productivity. Currently there are no scientifically validated therapies for relieving chronic pain. As a result, the health community targets 'pain management' where multi-modal therapies are used concurrently with the hope of providing some improvement in quality of life. Thus, there is an urgent need for drugs that can relieve chronic pain.

SUMMARY OF THE INVENTION

The present invention answers this need by providing a method for treating chronic pain in an individual suffering from chronic pain, comprising administering to the individual an amount of a therapeutic comprising glycine receptor agonist or glycine transporter antagonist in an amount effective to treat the chronic pain. In specific embodiments, the therapeutic comprises D-cycloserine and/or sarcosine. The therapeutic may also contain a secondary analgesic such as opiates, NSAIDs, and cox-2 inhibitors.

The invention also provides a pharmaceutical composition in the form of an injectable solution comprising at least two different analgesics, wherein at least one of the analgesics is a glycine receptor agonist or a GlyT-1 glycine transporter antagonist. Suitable pharmaceutical compositions comprise D-cycloserine and/or sarcosine, optionally in combination with opiates, NSAIDs, and cox-2 inhibitors.

BRIEF DESCRIPTION OF THE DRAWINGS

The invention will be described with respect to a drawing in several figures.

DETAILED DESCRIPTION OF THE INVENTION

Definitions

Figure 1:
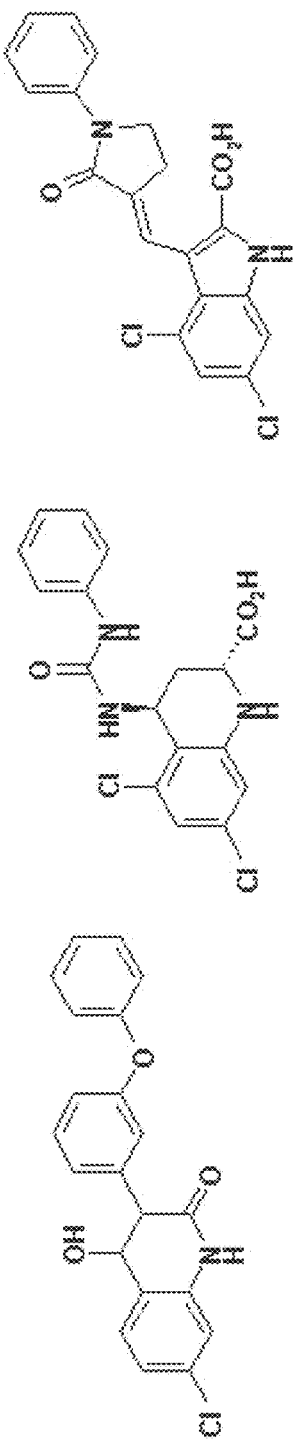
FIG. 1 shows structures of glycine receptor agonists.

As used in the specification and claims of this application, the following terms should be understood to have the following meaning:

"chronic pain" refers to pain that persists even after healing or a cure of an underlying condition has been achieved. In this case, the brain continues to perceive pain, even though there is no apparent injury or cause. Thus, chronic pain is pain which persists following normal healing time, for example beyond 3 months after an injury. Chronic pain may include pain associated with cancer or cancer treatments, persistent and degenerative conditions, and neuropathy, or nerve damage.

"administering" refers to the process of introducing a therapeutic agent into an individual to be treated. The route of administration may be tailored to the need of the individual. However, in general administration via topical, nasal or oral administration, or by systemic routes such as parenteral, intramuscular or intravenous injection is suitable. Administration may be done spatially proximate to the location of the perceived chronic pain, although since the mechanism of action is believed to be centered in the cerebral cortex, such administration would either be relying on a placebo affect, or include a supplemental analgesic.

"an amount effective to treat" is an amount that results in a reduction in the chronic pain as experienced by the individual for a period of time. Complete elimination of the pain is not required, nor is permanence of the reduction.

the "individual" being treated is a mammal suffering from chronic pain. Frequently, the individual will be a human. However, the invention is also applicable to other mammals, notably animals such as dogs, cats, and horses.

the term "glycine receptor agonist" refers to a compound that is at least a partial agonist of the glycine binding site of the N-methyl-D-aspartate ("NMDA") receptor. An agonist produces the same affect as glycine on the receptor.

"GlyT-1 glycine transporter antagonist" or "glycine transporter antagonist" refers to a molecule that interacts with the GlyT-1 glycine transporter to inhibit transport of glycine. GlyT-1 is also known as the sodium and chloride dependent transporter 1.

Mechanistic Basis for the Invention

Current pharmacology of pain pursues peripheral afferent conduction of nociceptive information and spinal cord manipulations for pain control. Such an approach, however, fails to effectively address chronic pain. For example, research conducted in humans and rodents indicates that a large proportion of neuropathic pain, a form of chronic pain, is supraspinal.

Specifically, Applicant's studies in humans with chronic pain, chronic back pain, post herpetic neuropathy, complex regional pain syndrome, indicate that medial prefrontal cortex is activated with the chronic pain, reflecting the intensity of this pain. Moreover, this activity is mediated through thalamic-prefrontal-amygdala circuitry. Therefore, chronic pain can be viewed as a pain conditioned state with inability to extinguish. Apkarian et al. Am. Pain Soc. Abstracts 2003. Apkarian et al. Soc. Neurosci. Abstracts 2003. Apkarian et al. Neurosci. Lett., 311, 193 (2001).

Treatment of pain as a conditioned state has not been reported. However, extinguishing of other conditioned states, notably fear, using therapeutic agents has been studied. Recent studies in other labs have shown that the medial frontal cortex is involved in extinction of fear conditioning, and that enhancing or blocking the glycine receptor in the medial frontal cortex can respectively increase or eliminate extinction. Walker D L et al. J. Neurosci 22, 2343 (2002); Santini E et al. J. Neurosci. 21, 9009 (2001); Morrow B A et al. J. Neurosci. 19, 5666 (1999), Herry C et al. J. Neurophys. 85, 2827 (1999); Morgan A M and LeDoux J E, Beh Neurosci. 109, 681 (1995); Quirk G J et al. J. Neurosci 20, 6225 (2000); Milad M R and Quirk G J, Nature 420, 70 (2002).

The present invention applies the mechanisms for extinction of fear conditioning to extinction of pain conditioning. Thus, in accordance with the present invention, compounds that act as glycine receptor agonists or glycine transporter antagonists are used as therapeutics for treatment of chronic pain.

Examples of Glycine Receptor Agonists

A primary example of a glycine receptor agonist is D-cycloserine. D-cycloserine is an analog to D-alanine. It has antibiotic activity against Gram-negative bacteria. See: Stammer C H, et al. J. Am. Chem. Soc. 77, 2346 (1995). El-Obeid H A and Al-Badr A A, In: Analytical profiles of drug substances, vol: 18, p. 567 (Academic Press, NY, 1989). Kuehl F A, Jr, et al. J. Am. Chem. Soc. 77, 2344 (1955). D-cycloserine is an excitatory amino acid and partial agonist at the glycine binding site of the NMDA receptor. At low doses, it enhances learning and memory. At high-doses, it is utilized as an anti-convulsant. See: Schneider J S et al, Brain Res. 860, 190 (2000). Wlaz P et al. Epilepsia 37, 610 (1996). Nakazato E, et al. Life Sci. 67, 1139 (2000). Pitkanen M et al., J. Neual Transm Park Dis Dement 9, 133 (1995). Disterhoft J F et al, Soc Neurosci Abstracts 2003. D-cycloserine is reported to relieve symptoms of opioid withdrawal. See: Oliveto A. et al., Exp Clin Psychopharmacol 11, 237 (2003). D-cycloserine has also been tested in schizophrenia, autism, anxiety disorders, and Alzheimer's disease. D-cycloserine has also been shown to be an effective agent for extinguishing fear conditioning in rodents when administered systemically or in the amygdala.

Because D-cycloserine is a known therapeutic with existing toxicology data, it is an attractive molecule for use in the method of the present invention. There are, however, other glycine receptor agonists. For example, the compositions shown in FIG. 1 are reported to act as glycine receptor agonists. http://www.bris.ac.uk/Depts/Synaptic/info/pharmacology/MDA.html.

D-serine and D-alanine may also be used in the method of the present invention.

U.S. Pat. No. 6,667,297, which is incorporated herein by reference, discloses methods for treating neuropsychiatric disorders using therapeutic agents that interact with the glycine receptor. The therapeutic agents of this disclosure are suitably used in the method of the present invention.

In addition to the specific compounds, pharmaceutically acceptable salts or esters may be employed. In addition, precursor compounds that are converted (e.g. metabolized) into the active agent in vivo can be employed. For example, D-alanine, D-serine, and/or D-cycloserine and/or N-methylglycine can be substituted with a modified version of the amino acid, such as a salt, ester, alkylated form, or a precursor of the amino acid. For example, the amino acid can be in the form of a sodium salt, potassium salt, calcium salt, magnesium salt, zinc salt, or ammonium salt. Such salt forms of D-serine, D-alanine, N-methylglycine and D-cycloserine can be made in accordance with conventional methods (see, e.g., Organic Chemistry, pgs. 822-823, Morrison and Boyd, ed., Fifth Edition, Allyn and Bacon, Inc., Newton, Mass.). Other modified forms of D-serine, D-alanine, N-methylglycine and D-cycloserine also can be used in the methods of the invention. For example, the carboxy group of the amino acid can be converted to an ester group by reaction with an alcohol in accordance with standard esterification methods (Id. at 841-843). For example, alcohols having 1-20 carbon atoms can be used to produce an ester of D-serine, D-alanine, N-methylglycine or D-cycloserine for use in the invention (e.g., methyl-, ethyl-, propyl-, isopropyl-, butyl-, isobutyl-, sec-butyl-, tert-butyl-, pentyl-, isopentyl-, tert-pentyl-, hexyl-, heptyl-, octyl-, decyl-, dodecyl-, tetradecyl-, hexadecyl-, octadecyl-, and phenyl-alcohols can be used). In another variation, the amino group of the amino acid can be alkylated, using conventional methods, to produce a secondary or tertiary amino group by ammonolysis of halides or reductive amination (Id. at 939-948). For example, an alkyl group having 1-20 carbon atoms can be added to the amino acid to produce an alkylated amino acid (e.g., methyl-, ethyl-, propyl-, isopropyl-, butyl-, isobutyl-, sec-butyl-, tert-butyl-, pentyl-, isopentyl-, tert-pentyl-, hexyl-, heptyl-, octyl-, decyl-, dodecyl-, tetradecyl-, hexadecyl-, octadecyl- and phenyl-groups can be added to the amino acid). D-phosphoserine and L-phosphoserine are examples of precursors of D-serine, and are commercially available (e.g., from Sigma Chemical, St. Louis, Mo.). N,N,N-trimethylglycine (betaine) and N,N-dimethylglycine are examples of precursors of N-methylglycine.

Examples of Glycine Transporter Antagonists

As an alternative to the use of a glycine receptor agonist, compounds that oppose glycine transport via the GlyT-1 transporter can also be employed in the method of the invention. Non-limiting examples of glycine transporter antagonists include N-methyl glycine, sarcosine, and sarcosine derivatives such as N[3-(4"-fluorophenyl)-3-(4"-phenylphenoxy)propyl]sarcosine, described in Herdon et al., Neuropharmacology. 2001 July; 41(1):88-96. See also WO 97/45115, which is incorporated herein by reference. Spiro (2h-1-benzopyran-2,4-piperidine) derivatives may also be used as GlyT-1 inhibitors as described in U.S. Pat. No. 6,645,973 which is incorporated herein by reference. Glycyldodecylamide (GDA) is identified as a glycine transport inhibitor on U.S. Pat. No. 5,837,730. which is incorporated herein by reference.

U.S. Pat. No. 6,361,957, which is incorporated herein by reference discloses an assay system for identifying glycine transport antagonists.

Preparation of cells expressing GyT-1 transporter sequences that can be used in assaying for inhibitors is disclosed in U.S. Pat. No. 6,251,617, which is incorporated herein by reference.

In addition to the specific compounds, pharmaceutically acceptable salts or esters may be employed. In addition, precursor compounds that are converted (e.g. metabolized) into the active agent in vivo can be employed. For example, in the in case of N-methyl glycine, suitable precursors are N,N,N-trimethylglycine (betaine), or N,N-dimethylglycine).

Method of the Invention

In accordance with the method of the invention, a glycine receptor agonist or a GlyT-1 glycine transporter antagonist is administered to an individual, including a human individual, suffering from chronic pain. The therapeutic agent is administered in an amount sufficient to be effective, without inducing toxicity or saturating the system such that the agent loses efficacy. The specific amounts will depend on various factors including the therapeutic agent employed (higher specific activity=lower dose), mode of administration (more immediate administration to the brain/greater ability to pass the blood brain barrier=lower dose), and frequency of administration (continuous or more frequent administration=lower dose), and the determination of appropriate dosages is within the skill in the art.

As observed in U.S. Pat. No. 6,667,297, typically, a dosage of 100 μg to 100 g (e.g., 1 mg to 100 g; 1 mg to 100 mg; 10 mg to 100 g; 10 mg to 10 g; or 10 to 500 mg) is suitable for D-alanine, D-serine, and N-methylglycine. D-cycloserine is administered at a dosage of 10 to 1000 mg, for example 100 to 500 mg, to human patients. When the patient is treated with both D-serine and D-alanine, D-serine and D-alanine can be administered to the patient simultaneously or sequentially, e.g., by formulating the D-serine and D-alanine as a single pharmaceutical composition or as two or more pharmaceutical compositions. Likewise, the patient can be treated with both D-serine and D-cycloserine, or D-serine and N-methylglycine, or D-alanine and N-methylglycine, or D-cycloserine and N-methylglycine simultaneously or sequentially. In one, but not the only, suitable method of treatment, the pharmaceutical composition is administered to the patient at least once daily for at least one week. If desired, the pharmaceutical composition can be administered to the patient in more than one dose per day (e.g., 2, 3, or 4 doses). Generally, the patient is treated for at least one week; typically, the patient is treated for at least several weeks (e.g., at least 4, 6, or 8 weeks) or months (e.g., at least 4, 8, or 12 months). If necessary, the treatment can continue indefinitely to keep the patient's symptoms under control throughout his or her life. These same amounts and protocols can be used in the method of the present invention.

By way of particular example, in the case where the therapeutic agent being administered is D-cycloserine, the following protocols are appropriate and are being implemented as Phase II clinical trials.

Protocol for Post-Herpetic Neuraligia

To treat post-herpetic neuralgia in human patients, 100 mg D-cycloserine in tablet form is taken once daily (generally at night) for a period of 1 week, to confirm patient tolerance to the treatment. If side effects/tolerance are acceptable, the dosage may be increased to 100 mg, twice daily, (generally morning and night) as needed for pain. Additional gradual dosage increases subject to tolerance may be made as needed to control pain to a daily maximum dosage of 1 g.

Chemotherapy-Induced Peripheral Neuropathic Pain

To treat chemotherapy-induced pain in human subjects, for example pain following chemotherapy treatment with 2 mg/kg twice weekly cisplatin, 250 mg D-cycloserine in tablet form is taken once daily. Increased dosage to a maximum of 1 g per day may be used, preferably in temporally-separate doses spread over the day. Concurrent usage of opiates or other pain killers may be made, although the goal is the reduction in the usage of opiate and similar pain killers. This same type of therapy could be used for treatment of pain following administration of pain following administration of taxanes.

Chronic Low Back Pain

To treat chronic low back pain in human subjects, 250 mg D-cycloserine in tablet form is taken once daily. Increased dosage to a maximum of 1 g per day may be used, preferably in temporally-separate 250 mg doses, i.e., 3 to 4 times per day.

In the method of the invention, combinations of two or more glycine receptor agonists and/or GlyT-1 glycine transport antagonists can be employed. Furthermore, the additional analgesics may be suitably used in combination with a glycine receptor agonists and/or a GlyT-1 glycine transport antagonists, or a combination thereof. Suitable analgesics include, without limitation, opiates, NSAIDs, and cox-2 inhibitors. These analgesics may be used at the same or lower dosages as in conventional pain management, since the combination should potentiate the effects of either treatment used alone.

Pharmaceutical Compositions

The invention also provides a pharmaceutical composition in the form of an injectable solution comprising at least two different analgesics, wherein at least one of the analgesics is a glycine receptor agonist or a GlyT-1 glycine transporter antagonist. Suitable pharmaceutical compositions comprise D-cycloserine and/or sarcosine, optionally in combination with opiates, NSAIDs, and cox-2 inhibitors. Examples of opiates include without limitation Opium, Codeine, Morphine, Heroin, Hydromorphone (Dilaudid), Oxycodone (Percodan), Oxymorphone (Numorphan), Hydrocodone (Vicodin), Meperidine (Demerol), Fentanyl, Methadone (Dolophine), Darvon, Talwin. Examples of NSAIDs include without limitation aspirin, ibuprofen, naproxen and nabumetone. Examples of cox-2 inhibitors include without limitation celecoxib, etoricoxib, rofecoxib, lumiracoxib and valdecoxib.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated. Tablet compositions can also be formulated using techniques known in the art. By way of non-limiting example, oral formulations providing 25 to 250 mg of D-cycloserine for administration one or more times per day are suitable.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

In formulating injectable solutions, it will be recognized that the greater the concentration, the lower the volume that needs to be injected to attain the same dosage. Accordingly, it is desirable to have the solution as concentrated as possible, bearing in mind solubility of the therapeutic agent and the need to avoid a shock effect at the point of administration if the solution is too concentrated.

The invention will now be further described with reference to the following non-limiting examples.

Example 1

Rats with mechanically injured paws were used as models of neuropathic pain. In the test, a weight is applied to the injured paw, and the pain response is assessed. More effective pain control allows the rat to tolerate a greater weight. Rats (groups or 8-10 rats per treatment) were treated with oral saline (control) or 3, 10 or 30 mg/kg of D-cycloserine for a period of two weeks. Pain was monitored from two days before the treatment commenced for a period of 35 days total.

Figure 2A:
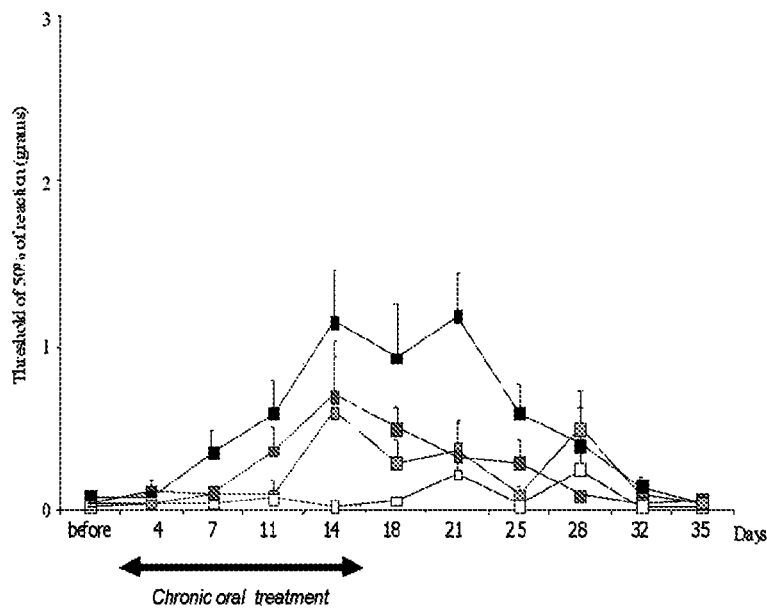
FIGS. 2A-C show results from tests of D-cycloserine in a rat model for neuropathic pain due to injury.

FIG. 2A shows a graphical representation of the results of this study, with the period of oral treatment with D-cycloserine shown in the shaded region. The open squares represent the control. The black squares represent 30 mg/kg dosage. The two intermediate lines are 3 (lighter) and 10 mg/kg (darker). As can be seen, during the time of treatment, there is a generally dose-dependent response. Post-treatment, the animals show long-lasting analgesia, with a return to initial neuropathy levels at day 35.

Figure 2B:
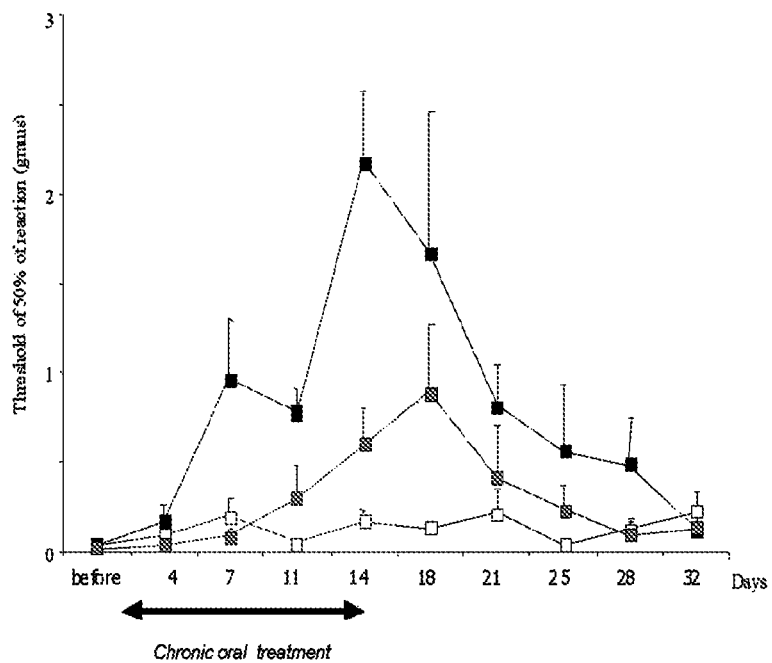

FIG. 2B shows a graphical representation of results when the rats originally treated with 30 mg/kg were retreated with 30 mg/kg of D-cycloserine commencing 1 day after the end of the original 35 day test. The black squares are the retreated animals, the white squares are the controls and the intermediate colored squares are animals treated for the first time with 30 mg/kg. As shown, the analgesic effectiveness is about twice as great on re-treatment.

Figure 2C:
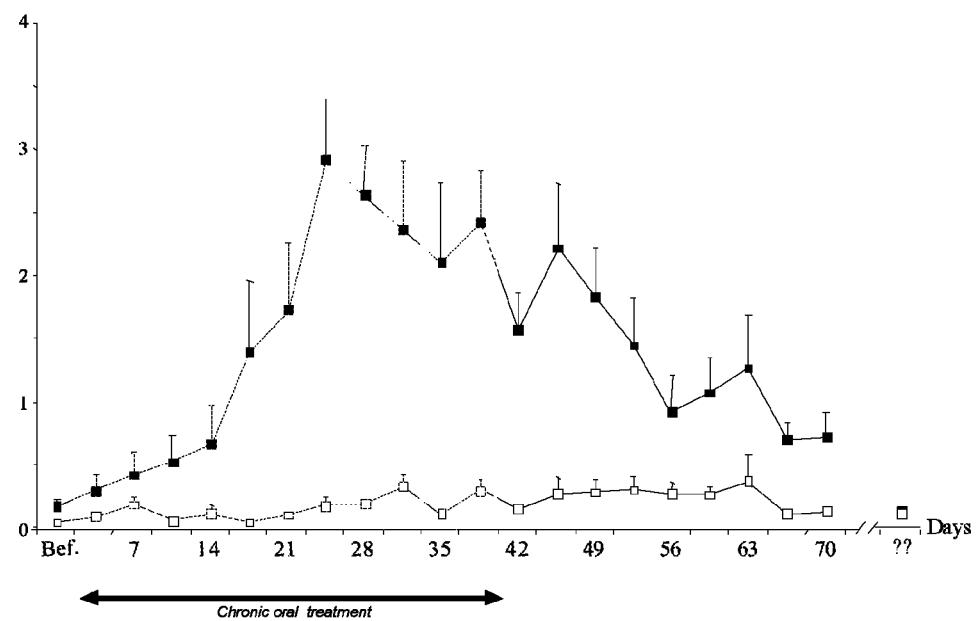

FIG. 2C shows results from a longer treatment period at a dosage of 30 mg/kg. As shown, the analgesic effect increases with treatment for a period of three weeks, after which a plateau is reached. Further, the animals that are treated for a longer period show a longer post treatment duration of analgesia, with significant analgesic affect being observed 30 days after cessation of treatment.

Figure 3A:
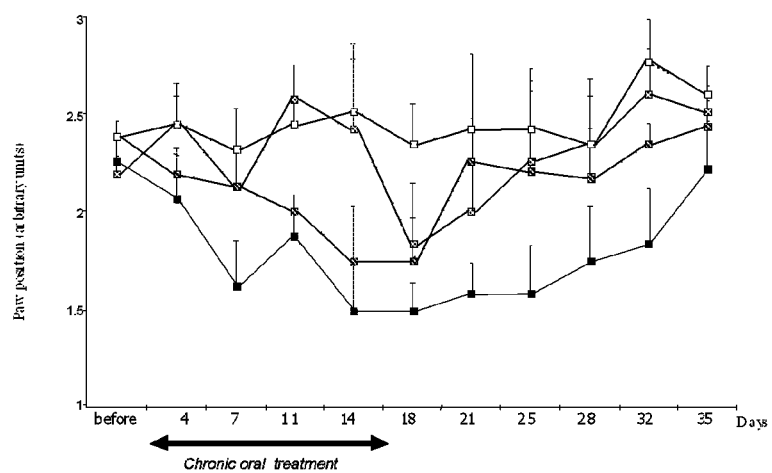
FIG. 3A-C show results from tests of D-cycloserine in a rat model for neuropathic pain due to injury.
Figure 3B:
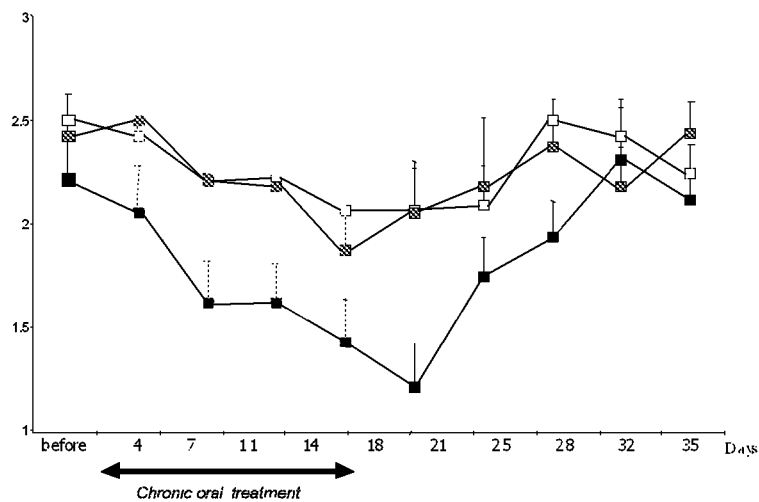
Figure 3C:
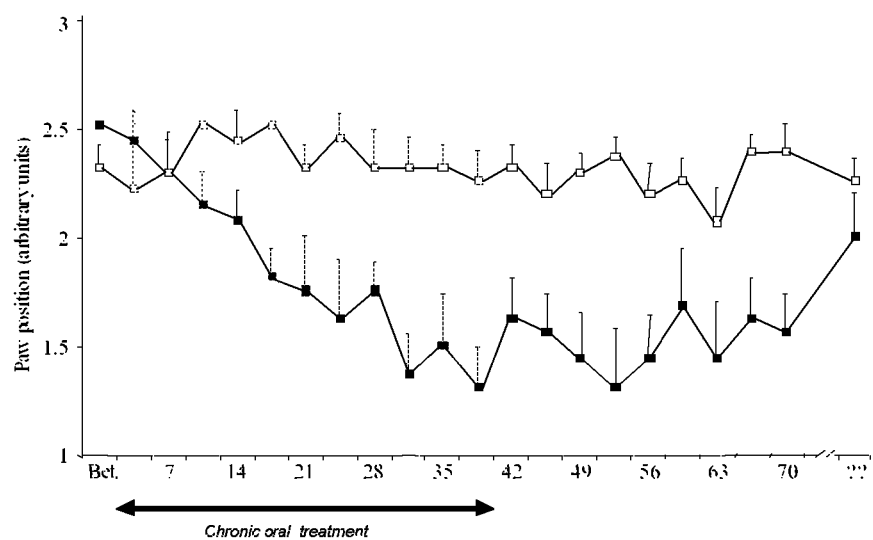

FIGS. 3A-C show results for the same test animals as FIGS. 2A-C, except using a test based on paw position as opposed to tolerance to applied weight. In this case, lower numbers reflect lesser pain. As can be seen, this measure of pain also indicates the effectiveness of the D-cycloserine.

Acute oral or intrathecal administration of D-cycloserine had only minimal analgesic effects on the neuropathic behavior observed in this rat model. Thus, treatment of chronic pain requires a treatment regimen that extends over a period of time, for example at least one week, sufficient to provide a benefit to the individual being treated.

Example 2

Figure 4:
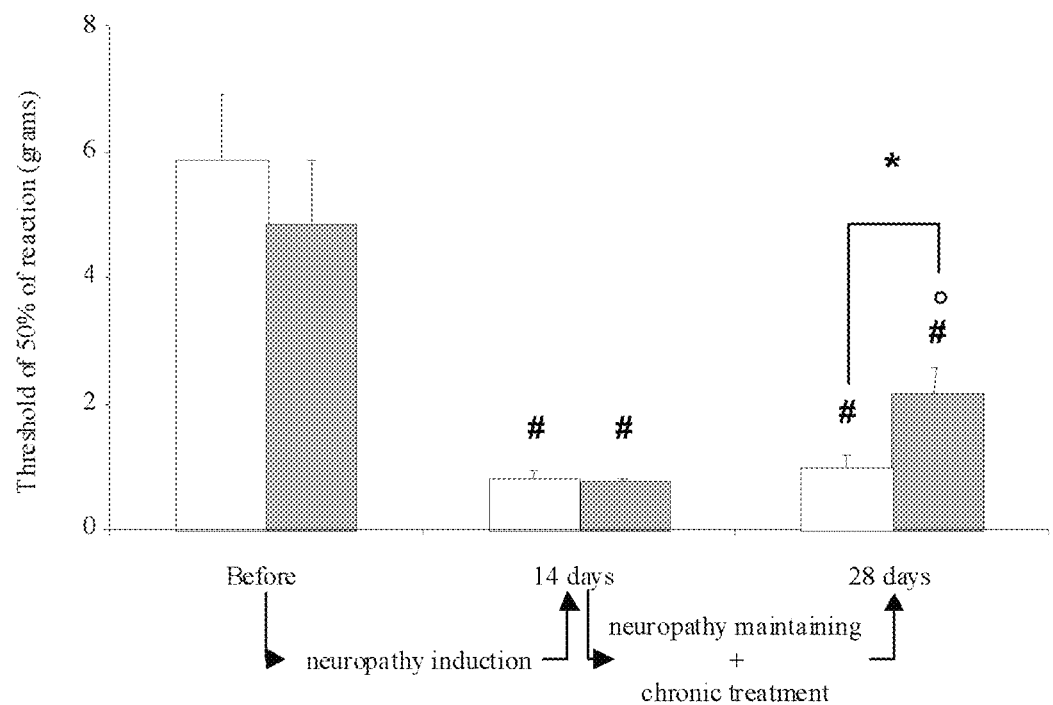
FIG. 4 shows effects of D-cycloserine in a rat model of drug-induced neuropathy.

To model drug-induced pain, rats were treated with cisplatin (2 mg/kg), a common chemotherapy drug. As shown graphically in FIG. 4, after 14 days of treatment, the rats had developed mechanical sensitivity. In the next 14 days of treatment with cisplatin, oral treatment with 30 mg/kg of D-cycloserine, two treatments per day, result in a partial reversal of the mechanical sensitivity (gray bars). In contrast, sensitivity was maintained in rats treated with a saline control (white bars). Thus, in rat models of cisplatin-induced neuropathy, pain behavior decreases 50% in two weeks in animals treated with cycloserine compared with animals treated with placebo.

Example 3

Figure 5:
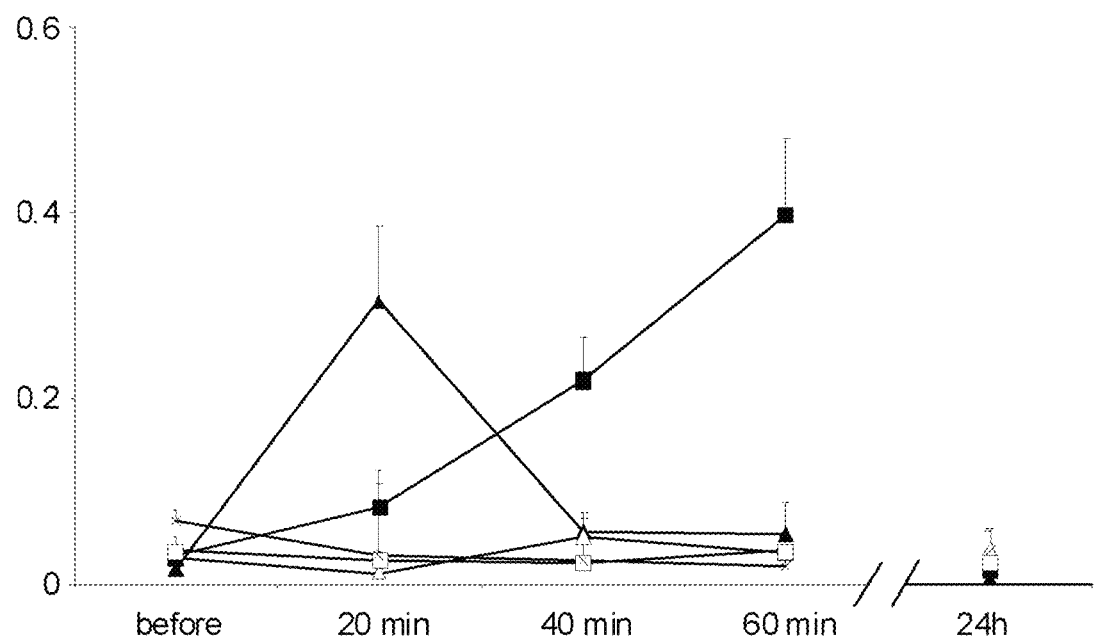
FIG. 5 shows analgesia following infusion of D-cycloserine into different parts of a rat brain.

FIG. 5 shows the effects of infusing D-cycloserine (50 μg) into the medial prefrontal cortex (black squares), bilateral amygdala (black triangles), and visual cortex (white triangles) as compared to a saline infusion in the medial prefrontal cortex (white squares) in a rat exhibiting mechanical sensitivity Only medial prefrontal cortex and amygdala infusions result in analgesia.

What is claimed is:

1. A method for treating chronic pain in an individual in need thereof comprising administering to the individual a composition comprising D-cycloserine in an amount of 10 to 1000 mg at least once per day and for a period of time of at least 4 weeks.

2. The method of claim 1 wherein the composition is administered at least twice a day.

3. The method of claim 1, further comprising the step of co-administering a secondary analgesic different from the D-cycloserine.

4. The method of claim 3, wherein the secondary analgesic is an opiate, non-steroidal anti-inflammatory (NSAID) or cyclooxygenase-2 (cox-2) inhibitor.

5. The method of claim 1, wherein the individual is a human.

6. The method of claim 1, wherein the D-cycloserine is administered orally.

7. The method of claim 6, further comprising the step of co-administering a secondary analgesic different from the D-cycloserine.

8. The method of claim 7, wherein the secondary analgesic is an opiate, NSAID or cox-2 inhibitor.

9. The method of claim 1, wherein the composition consists of D-cycloserine and a pharmaceutically acceptable carrier or excipient.

10. The method of claim 1, wherein D-cycloserine is administered nasally.

11. The method of claim 1, wherein D-cycloserine is administered intravenously.

12. The method of claim 1, wherein said chronic pain is characterized as having persisted in the individual for more than three months.

13. The method of claim 1, wherein said chronic pain is selected from post-herpetic neuralgia, neuropathic pain, chronic low back pain, and mechanical sensitivity.

14. The method of claim 13, wherein said neuropathic pain is chemotherapy-induced peripheral neuropathic pain.

15. The method of claim 1, wherein said administering is for a period of time of at least 6 weeks.

16. The method of claim 15, wherein said administering is for a period of time of at least 8 weeks.

17. The method of claim 16, wherein said administering is for a period of time of at least several months.

18. The method of claim 17, wherein said administering is for a period of time of at least 4 months.

19. The method of claim 18, wherein said administering is for a period of time of at least 8 months.

20. The method of claim 19, wherein said administering is for a period of time of at least 12 months.

* * * * *